US009651526B2

(12) United States Patent
Aoki et al.

(10) Patent No.: US 9,651,526 B2
(45) Date of Patent: May 16, 2017

(54) LIQUID CHROMATOGRAPH (71) Applicant: SHIMADZU CORPORATION, Kyoto-shi, Kyoto (JP)

(72) Inventors: Kengo Aoki, Kyoto (JP); Keisuke Ogawa, Kyoto (JP)

(73) Assignee: SHIMADZU CORPORATION, Kyoto-shi (JP)

( * ) Notice: Subject to any disclaimer, the term of this patent is extended or adjusted under 35 U.S.C. 154(b) by 15 days.

(21) Appl. No.: 14/668,000

(22) Filed: Mar. 25, 2015

(65) Prior Publication Data
US 2015/0276688 A1 Oct. 1, 2015

(30) Foreign Application Priority Data

Mar. 31, 2014 (JP) ................. 2014-073103

(51) Int. Cl.
G01N 30/34 (2006.01)
B01D 15/16 (2006.01)
B01D 15/18 (2006.01)
B01D 15/08 (2006.01)
G01N 30/20 (2006.01)
(Continued)

(52) U.S. Cl.
CPC ............ G01N 30/34 (2013.01); B01D 15/08 (2013.01); B01D 15/16 (2013.01); B01D 15/166 (2013.01); B01D 15/18 (2013.01); G01N 30/20 (2013.01); G01N 30/8658 (2013.01); G01N 30/8675 (2013.01); G01N 30/8665 (2013.01); G01N 2030/347 (2013.01); G01N 2030/383 (2013.01); G01N 2030/385 (2013.01)

(58) Field of Classification Search
CPC ............ G01N 30/34; G01N 2030/385; G01N 2030/383; G01N 2030/347; B01D 15/16; B01D 15/166; B01D 15/18
See application file for complete search history.

(56) References Cited

FOREIGN PATENT DOCUMENTS

JP 2002-277451 A 9/2002
JP 2004-093251 A 3/2004

OTHER PUBLICATIONS

Office Action dated Mar. 8, 2016, issued in counterpart Chinese Patent Application No. 201510144365.6, with English translation. (19 pages).

(Continued)

Primary Examiner — Paul West
(74) Attorney, Agent, or Firm — Westerman, Hattori, Daniels & Adrian, LLP (57) ABSTRACT A liquid chromatograph has a mobile phase delivery section including, between mobile phase channels connected respectively to a plurality of mobile phase containers and a delivery pump, channel switching valves for selecting one of the mobile phase channels. This liquid chromatograph whose channel switching valves have a hierarchical structure including at least two stages includes a valve connection state setting section that is configured to set the connection state between the channel switching valves and the connection state between the channel switching valves and the mobile phase channels, and further includes a per channel total delivery amount calculation section that is configured to calculate the total delivery amount of mobile phase per mobile phase channel based on a connection state according to the valve connection state setting section, the delivery amount per unit time by the delivery pump, and the operation time of the delivery pump.

7 Claims, 4 Drawing Sheets

(51) Int. Cl.
   *G01N 30/38*    (2006.01)
   *G01N 30/86*    (2006.01)

(56) References Cited

OTHER PUBLICATIONS

Decision of Rejection dated Nov. 7, 2016, issued in counterpart Chinese Application No. 201510144365.6, with English translation. (17 pages).

LIQUID CHROMATOGRAPH

BACKGROUND OF THE INVENTION

1. Field of the Invention

The present invention relates to a liquid chromatograph including an HPLC (high-performance liquid chromatograph), and also relates to an analytical device including, as a part thereof, a liquid chromatograph, such as an LCMS (liquid chromatograph mass spectrometer).

2. Description of the Related Art

In a liquid chromatograph, in order to switch between and send several types of mobile phases to an analysis channel, a channel switching valve is connected to a delivery pump, and switching among several mobile phases is enabled with respect to one delivery pump (see JP 2002-277451 A).

Channel switching valves are referred to as a first-stage channel switching valve, a second-stage channel switching valve, etc. in the order from the one closest to the pump (on the downstream side). Whereas the first-stage channel switching valve is provided to the liquid chromatograph as pre-installed equipment, the second-stage channel switching valve is an optional channel switching valve that is connected by a user to one of the ports of the first-stage channel switching valve. It is also possible to connect third- and later-stage channel switching valves, and these are also optional channel switching valves.

According to such a delivery system, the total delivery amount of mobile phases and the remaining amount of mobile phases are calculated by the following method.

(1) The type (the number of ports) and connection/non-connection of the first-stage channel switching valve are set to a channel control section. Since the first-stage channel switching valve is a pre-installed structural element, some channel control sections are enabled to automatically recognize the type and connection/non-connection of the first-stage channel switching valve. However, with respect to the optional second- and later-stage channel switching valves, setting of the types and connection/non-connection thereof is not performed.

(2) The total amount of mobile phase is set for the mobile phase connected to each mobile phase channel.

(3) A delivery control section calculates the total delivery amount of each channel connected to the first-stage channel switching valve based on the delivery flow rate of the pump and the open time of each port of the first-stage channel switching valve.

(4) The total delivery amount is subtracted from the total amount of mobile phase, and the remaining amount of mobile phase of each channel connected to the first-stage channel switching valve is determined.

With a conventional liquid chromatograph, even when the second- and later-stage channel switching valves are connected, only the total delivery amount of each channel connected to the first-stage channel switching valve may be calculated, and it is not possible to determine the total delivery amount of each mobile phase connected to the port of the second- or later-stage channel switching valve.

SUMMARY OF THE INVENTION

An object of the present invention is to enable determination of the total delivery amount of each mobile phase connected to a port of a second- or later-stage channel switching valve.

A liquid chromatograph of the present invention is a liquid chromatograph including, along an analysis channel connected on a downstream of a mobile phase delivery section for sending a mobile phase by a delivery pump, a sample introduction section for introducing a sample into the analysis channel, a column for separating an introduced sample, and a detector for detecting a sample component separated by the column.

The mobile phase delivery section includes, between mobile phase channels connected respectively to a plurality of mobile phase containers and the delivery pump, channel switching valves for selecting one of the mobile phase channels, and the channel switching valves have a hierarchical structure where the channel switching valve on a lower stage side is connected to a port of the channel switching valve on an upper stage side, and the channel switching valve on an uppermost stage side is connected to the delivery pump.

The liquid chromatograph of the present invention further includes a program control section storing an analysis program, and a delivery control section configured to control an operation of the mobile phase delivery section according to an instruction from the program control section.

Furthermore, the liquid chromatograph of the present invention includes a valve connection state setting section configured to set a connection state between the channel switching valves and a connection state between the channel switching valves and the mobile phase channels, and a per channel total delivery amount calculation section configured to calculate a total delivery amount of mobile phase per mobile phase channel based on a connection state according to the valve connection state setting section, a delivery amount per unit time by the delivery pump, and an operation time of the delivery pump.

A mobile phase usually refers to a mobile phase for analysis use, but the mobile phase may alternatively be used for purging or rinsing of a channel. Also, a cleaning liquid is used to clean the channel. The mobile phase and cleaning liquid are delivered from the same mobile phase delivery section. Accordingly, in the present invention, the word "mobile phase" is used as a term referring not only to a mobile phase in a narrow sense, but also to a liquid that is delivered from the mobile phase delivery section, such as a cleaning liquid.

Since the liquid chromatograph of the present invention includes the valve connection state setting section configured to set a connection state between the channel switching valves and a connection state between the channel switching valve and the mobile phase channel, and the per channel total delivery amount calculation section configured to calculate a total delivery amount of mobile phase per mobile phase channel based on a connection state according to the valve connection state setting section, a delivery amount per unit time by the delivery pump, and an operation time of the delivery pump, even when a second- or later-stage channel switching valve is connected, the total delivery amount of each mobile phase may be determined.

Also, the total delivery amount of each mobile phase may be determined even when the connection state of the channel switching valve is changed according to the use of a user.

DETAILED DESCRIPTION OF THE PREFERRED EMBODIMENTS

Figure 1:
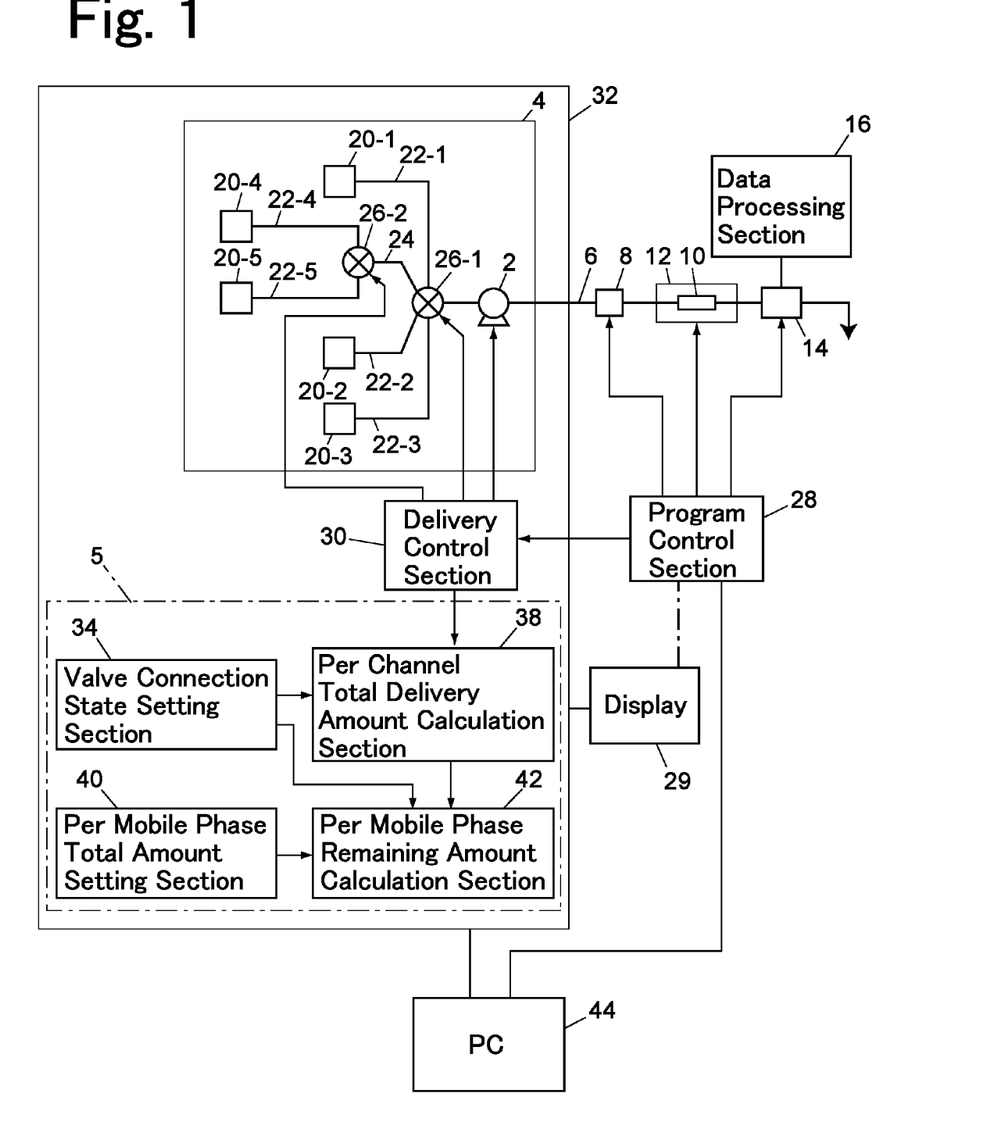
FIG. 1 is a block diagram showing a first embodiment.

An embodiment is shown in FIG. 1. An analysis channel 6 is connected on the downstream of a mobile phase delivery section 4 for sending a mobile phase by a delivery pump 2. Along the analysis channel 6, an automatic sample introduction section 8 for introducing a sample into the analysis channel 6, a column 10 for separating the introduced sample, and a detector 14 for detecting a sample component separated by the column 10 are arranged from the upstream of the flow of a mobile phase to the downstream. The column 10 is accommodated inside a column oven 12.

The mobile phase delivery section 4 includes, between mobile phase channels 22-1 to 22-5 connected respectively to a plurality of mobile phase containers 20-1 to 20-5 and the delivery pump 2, channel switching valves 26-1 and 26-2 for selecting one of the mobile phase channels 22-1 to 22-5.

In this embodiment, the channel switching valves 26-1 and 26-2 take the form of a hierarchical structure including two stages. The first-stage channel switching valve 26-1, which is the channel switching valve on the uppermost stage side, is connected to the delivery pump 2, and the second-stage channel switching valve 26-2 on the lower stage side is connected to one port of the channel switching valve 26-1 via a channel 24. In this embodiment, the first-stage channel switching valve 26-1 having four ports, and the second-stage channel switching valve 26-2 having two ports are used, but these are only examples, and the number of ports of the channel switching valves are arbitrary. Also, it is not necessary to use all the ports.

The first-stage channel switching valve 26-1 is a channel switching valve that is provided as a pre-installed structural element of the liquid chromatograph of this embodiment. On the other hand, the second-stage channel switching valve 26-2 is a channel switching valve that is externally attached at the request of a user, and may be connected to one of the ports of the first-stage channel switching valve 26-1. It is also possible to connect a third-stage channel switching valve, and the third-stage channel switching valve may be connected to one of the ports of the second-stage channel switching valve 26-2. Fourth- and later-stage channel switching valves may also be connected in a similar manner. The second- and later-stage channel switching valves are optional structural elements.

In this embodiment, to enable selection among five types of mobile phases and delivery thereof to the analysis channel 6, the mobile phase containers 20-1 to 20-5 for five types of mobile phases are provided, and the mobile phase channels 22-1 to 22-3 respectively connected to the mobile phase containers 20-1 to 20-3 for first to third mobile phases are connected to respective ports of the first-stage channel switching valve 26-1, and the mobile phase channels 22-4 and 22-5 respectively connected to the mobile phase containers 20-4 and 20-5 for fourth and fifth mobile phases are connected to respective ports of the second-stage channel switching valve 26-2.

To control the operation of this liquid chromatograph, a program control section 28 and a delivery control section 30 are provided. The program control section 28 stores an analysis program, and controls the operation of each section of the liquid chromatograph. The analysis program may include the types of mobile phases to be delivered and the delivery amount per unit time by the delivery pump 2.

The delivery control section 30 is configured to control the operation of the mobile phase delivery section 4 according to an instruction from the program control section 28. The delivery control section 30 may be configured as a separate structural element from the mobile phase delivery section 4, but in this embodiment, it is integrated with the mobile phase delivery section 4 to configure a pump unit 32. The pump unit 32 may be attached to the liquid chromatograph as one unit, and may be replaced.

The program control section 28 is a computer, and may be realized as a computer dedicated to the liquid chromatograph or as a general-purpose personal computer. An example of the dedicated computer is a system controller. In the case of realization by the system controller, connection to an external general-purpose personal computer 44 is enabled. The personal computer 44 may be connected only to the liquid chromatograph, or may be connected, via a network, to a plurality of analytical devices including the liquid chromatograph and other devices.

A data processing section 16 for processing a detected signal and generating a chromatogram, and for holding calibration curve data and determining the quantity of an analyzed component is connected to the detector 14. The data processing section 16 may be realized as a part of the program control section 28 or by the personal computer 44.

The delivery control section 30 is configured to control the operation of switching between the channel switching valves 26-1 and 26-2 and to control the operation of the delivery pump 2, according to instructions from the program control section 28.

The liquid chromatograph of this embodiment further includes a valve connection state setting section 34, a total delivery amount calculation section 38, a per mobile phase total amount setting section 40, and a per mobile phase remaining amount calculation section 42. A part 5 including the valve connection state setting section 34, the total delivery amount calculation section 38, the per mobile phase total amount setting section 40, and the per mobile phase remaining amount calculation section 42 may be realized wholly or partially by a dedicated computer, the pump unit 32, the program control section 28, or the external personal computer 44. An example is shown here where the part 5 is realized by the pump unit 32.

The valve connection state setting section 34 is configured to set the number of ports of the channel switching valves 26-1 and 26-2, the connection state between the channel switching valves 26-1 and 26-2, and the connection state between the channel switching valve 26-1 or 26-2 and respective mobile phase channels 22-1 to 22-5. Specifically, in this embodiment, as the connection state, it is set so that the channel 24 connected to the second-stage channel switching valve 26-2 and the mobile phase channels 22-1 to 22-3 are connected to the ports of the channel switching valve 26-1, and the mobile phase channels 22-4 and 22-5 are connected to the ports of the second-stage channel switching valve 26-2. Not all the ports of the channel switching valves 26-1 and 26-2 have to have a channel connected thereto, and there may be ports to which nothing is connected.

Settings and changes of the connection state in the valve connection state setting section 34 are at least partially performed by the user. The first-stage channel switching valve 26-1 is a pre-installed structural element of the liquid chromatograph, and thus, connection of the mobile phase channels 22-1 to 22-3 to respective ports of the first-stage channel switching valve 26-1 may be automatically detected. However, settings of the connection state with respect to each port may all be performed by the user for the first-stage channel switching valve 26-1 and the second-stage channel switching valve 26-2. In this embodiment, it is assumed that settings of the connection states of all the ports is performed by the user.

Such settings or changes of the connection state may be performed on a screen by displaying a screen for issuing an instruction regarding the connection state on a display 29. The display 29 is connected to the pump unit 32 in a case where the valve connection state setting section 34 is provided to the pump unit 32, or to the program control section 28 in a case where the valve connection state setting section 34 is connected to the program control section 28, and may use the display of the personal computer 44 in a case where the valve connection state setting section 34 is realized by the personal computer 44.

Furthermore, in the case where the program control section 28 is a system controller and is connected to an independent personal computer 44 or a personal computer 44 on a network, settings or changes may be performed by accessing a setting screen on the display 29 connected to the system controller through a Web browser installed in the personal computer 44.

The per channel total delivery amount calculation section 38 is configured to calculate the total delivery amount of mobile phase per mobile phase channel based on the connection state according to the valve connection state setting section 34, the delivery amount per unit time by the delivery pump 2, and the operation time of the delivery pump 2. The delivery amount per unit time by the delivery pump 2 and the operation time of the delivery pump 2 may be obtained from the delivery control section 30 or by signals from the program control section 28.

The calculated total delivery amount of mobile phase for each mobile phase channel may be displayed on the display 29 connected to the pump unit 32 or to the program control section 28, or may be displayed on the display of the personal computer 44.

In this embodiment, the liquid chromatograph further includes the per mobile phase total amount setting section 40, which is configured to set the amount of mobile phase contained in each of the mobile phase containers 20-1 to 20-5, and the per mobile phase remaining amount calculation section 42, which is configured to calculate the remaining amount of each mobile phase by subtracting the total delivery amount of mobile phase through each of the mobile phase channels 22-1 to 22-5 calculated by the total delivery amount calculation section 38 from the amount of mobile phase in each of the mobile phase containers 20-1 to 20-5 set in the total amount setting section 40.

To set the amount of mobile phase contained in each of the mobile phase containers 20-1 to 20-5 in the per mobile phase total amount setting section 40, a screen for issuing an instruction regarding the connection state may be displayed on the display 29 and settings may be performed on the screen, as in the case of settings or changes of the connection state in the valve connection state setting section 34. The display 29 is connected to the pump unit 32 in a case where the total amount setting section 40 is provided to the pump unit 32, or to the program control section 28 in a case where the total amount setting section 40 is connected to the program control section 28, and may use the display of the personal computer 44 in a case where the total amount setting section 40 is realized by the personal computer 44.

In the case of setting of the amount of mobile phase as well, if the program control section 28 is a system controller and is connected to an independent personal computer 44 or a personal computer 44 on a network, the amount of mobile phase may be set by accessing a setting screen on the display 29 connected to the system controller through a Web browser installed in the personal computer 44.

The remaining amount of each mobile phase calculated by the remaining amount calculation section 42 may be displayed on the display 29 connected to the pump unit 32 or to the program control section 28, or on the display of the personal computer 44.

Figure 2:
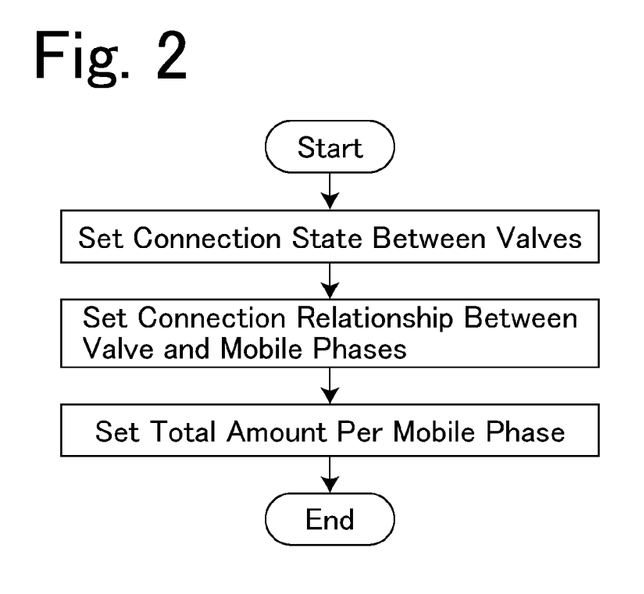
FIG. 2 is a flow chart showing a setting operation of the embodiment.

An operation according to this embodiment will be described. Settings are performed as shown in FIG. 2. A setting screen is displayed on the display 29 connected to the pump unit 32 or to the program control section 28, or on the display of the personal computer 44, and settings or changes are performed on the setting screen.

(1) To set the connection state between the channel switching valves 26-1 and 26-2, the number of ports of the first-stage channel switching valve 26-1, the number of ports of the second-stage channel switching valve 26-2, and to which port of the first-stage channel switching valve 26-1 the second-stage channel switching valve 26-2 is connected are set. In this embodiment, the first-stage channel switching valve 26-1 is a pre-installed structural element of the liquid chromatograph, and connection thereof to the delivery pump 2 is set in advance. Since the second-stage channel switching valve 26-2 is an externally-connected optional channel switching valve, the port of the first-stage channel switching valve 26-1 to which it is connected is set by the user.

(2) To which ports, among those set at the first-stage channel switching valve 26-1 and the second-stage channel switching valve 26-2, the mobile phase channels 22-1 to 22-5 are connected is set.

(3) The total amount of each mobile phase contained in each of the mobile phase containers 20-1 to 20-5 that are connected respectively to the connected mobile phase channels 22-1 to 22-5 is input and set.

When settings are done, an analysis operation may be performed. The mobile phase is consumed by the analysis operation, and thus, the total delivery amount of mobile phase through each of the mobile phase channels 22-1 to 22-5 and the remaining amounts in the mobile phase containers 20-1 to 20-5 are calculated for the mobile phases used, by the total delivery amount calculation section 38 and the remaining amount calculation section 42 in the manner shown in FIG. 3.

Figure 3:
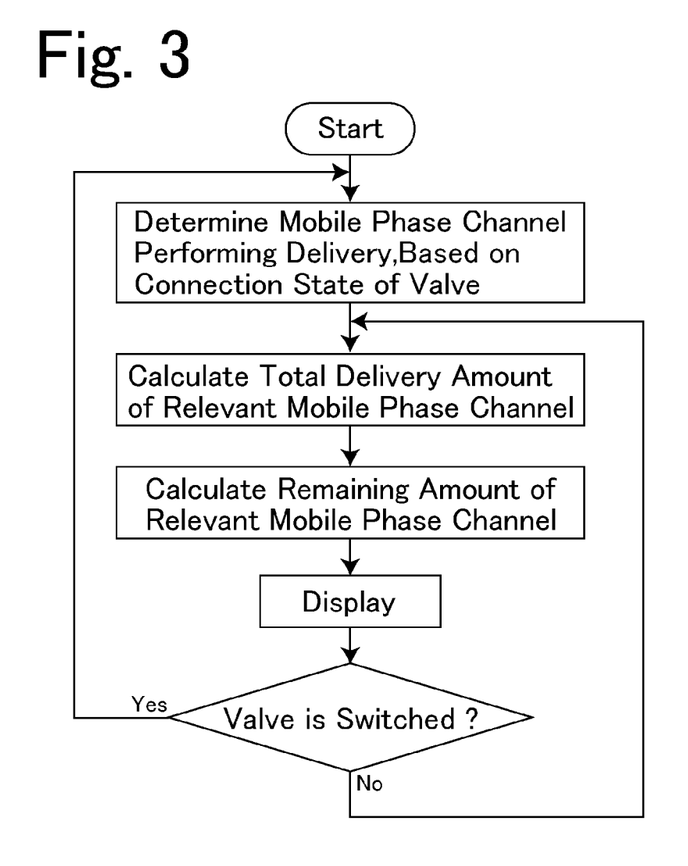
FIG. 3 is a flow chart showing an analysis operation of the embodiment.

The total delivery amount calculation section 38 determines the mobile phase channel performing delivery, based on the connection states of the ports of the channel switching valves 26-1 and 26-2, and integrates the delivery flow rate per unit time by the pump 2 over the open time of the channel switching valves 26-1 and 26-2 to calculate the total delivery amount through the mobile phase channel.

Furthermore, the remaining amount calculation section 42 calculates the remaining amount of the mobile phase by subtracting the calculated total delivery amount through the mobile phase channel from the total amount of the mobile phase that is set.

The total delivery amount and the remaining amount calculated for each mobile phase are displayed on the display.

In a case where analyses are performed continuously as well, if there is no switching of the mobile phase and the analysis is to be continued with the same mobile phase, the total delivery amount and the remaining amount of the mobile phase are calculated and displayed.

If one or both the first-stage channel switching valve 26-1 and the second-stage channel switching valve 26-2 are switched and the mobile phase is changed, the total delivery amount and the remaining amount of the new mobile phase are calculated and displayed in the same manner.

Figure 4:
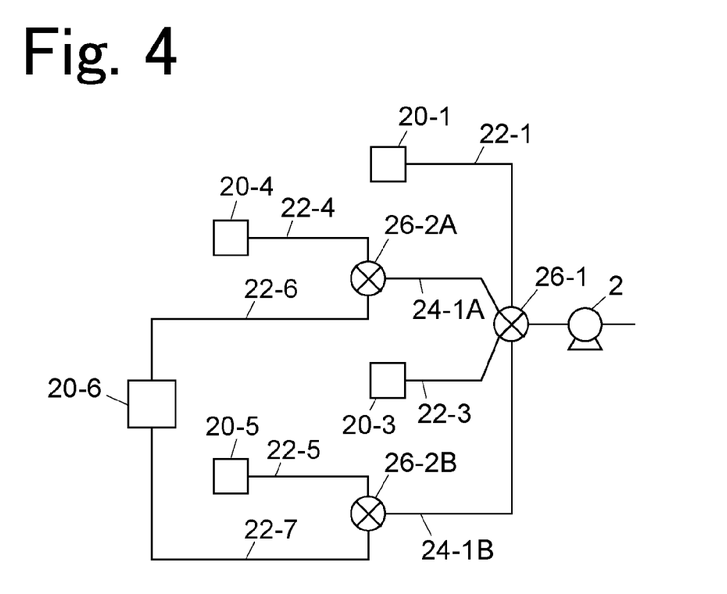
FIG. 4 is a channel diagram showing a mobile phase delivery section of a second embodiment.

FIG. 4 shows a mobile phase delivery section 4 of a second embodiment. The same structures as those of the mobile phase delivery section 4 of the embodiment in FIG. 1 will be denoted by the same reference signs, and detailed description thereof will be omitted.

This embodiment is a case where the mobile phases connected to a plurality of different channels are the same mobile phase. Second-stage channel switching valves 26-2A and 26-2B are connected to two ports of a first-stage channel switching valve 26-1 through channels 24-1A and 24-1B, respectively. A mobile phase channel 22-6 connected to one port of the channel switching valve 26-2A and a mobile phase channel 22-7 connected to one port of the channel switching valve 26-2B are connected to a common mobile phase container 20-6. This is a structure which is convenient in the case of using a common mobile phase in different channels. An example of such a common mobile phase is a cleaning liquid.

In this embodiment, a valve connection state setting section 34 is configured to include, as the setting value, connection of the plurality of mobile phase channels 22-6 and 22-7 to the one mobile phase container 20-6. Also, a total delivery amount calculation section 38 is configured to add up, with respect to the plurality of mobile phase channels 22-6 and 22-7 connected to the one mobile phase container 20-6, the total delivery amounts through these mobile phase channels to thereby calculate the same as the total delivery amount of one mobile phase channel.

Moreover, a remaining amount calculation section 42 is configured to subtract, with respect to the one mobile phase container 20-6 to which the plurality of mobile phase channels 22-6 and 22-7 are connected, the total delivery amount obtained by calculation based on addition from the amount of mobile phase in the mobile phase container 20-6 set in a total amount setting section 40 to thereby calculate the remaining amount of mobile phase in the mobile phase container 20-6.

According to such a configuration, it is not necessary to prepare separate containers containing the same mobile phase for each of the mobile phase channels 22-6 and 22-7, and the operability regarding replenishment of the mobile phase is improved.

Figure 5:
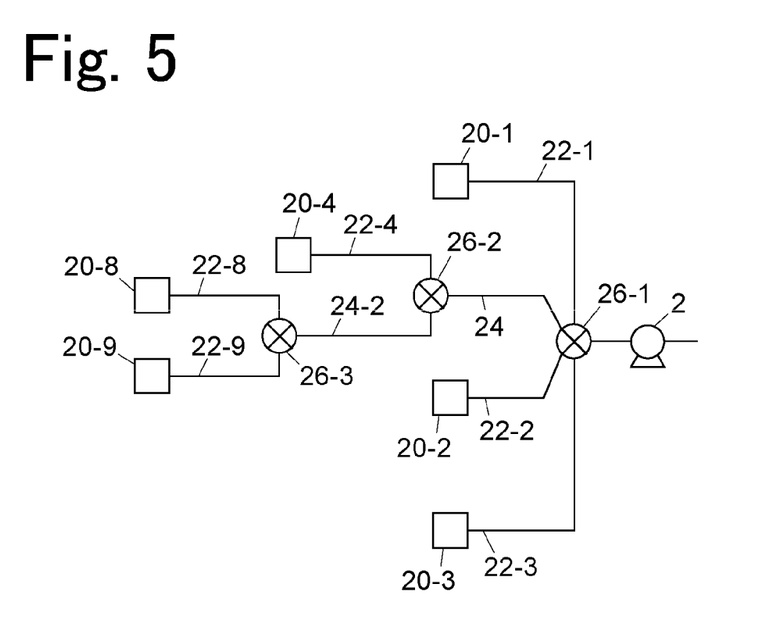
FIG. 5 is a channel diagram showing a mobile phase delivery section of a third embodiment.

FIG. 5 shows a mobile phase delivery section 4 of a third embodiment. The same structures as those of the mobile phase delivery section 4 of the embodiment in FIG. 1 will be denoted by the same reference signs, and detailed description thereof will be omitted.

This embodiment shows a case where the channel switching valves have a hierarchical structure including three stages. A second-stage channel switching valve 26-2 is connected to one port of a first-stage channel switching valve 26-1 via a channel 24, and a third-stage channel switching valve 26-3 is connected to one port of the second-stage channel switching valve 26-2 via a channel 24-2. Mobile phase containers are connected to other ports of the channel switching valves 26-1, 26-2 and 26-3 via respective mobile phase channels.

Fourth- and later-stage channel switching valves may be connected in the same manner. The second- and later-stage channel switching valves are external channel switching valves that may be optionally connected by the user.

In the case of connecting the channel switching valves in three or more stages in the above manner as well, settings in a valve connection state setting section 34 and a total amount setting section 40 may be performed in the same manner as in the embodiment in FIG. 1, and a per channel total delivery amount calculation section 38 and a per mobile phase remaining amount calculation section 42 also operate in the same manner.

What is claimed is:

1. A liquid chromatograph comprising:
   a mobile phase delivery section for sending a mobile phase by a delivery pump, the mobile phase delivery section including, between mobile phase channels connected respectively to a plurality of mobile phase containers and the delivery pump, channel switching valves for selecting one of the mobile phase channels, the channel switching valves having a hierarchical structure where the channel switching valve on a lower stage side is connected optionally to any input port of the channel switching valve on an upper stage side, the channel switching valve on an uppermost stage side being connected to the delivery pump;
   a sample introduction section for introducing a sample into an analysis channel connected on a downstream of the mobile phase delivery section;
   a column arranged on a downstream of the sample introduction section, for separating an introduced sample;
   a detector arranged on a downstream of the column, for detecting a sample component separated by the column;
   a program control section storing an analysis program;
   a delivery control section configured to control an operation of the mobile phase delivery section according to an instruction from the program control section;
   a valve connection state setting section configured to set a connection state of the channel switching valve on a lower side to the channel switching valve on an upper stage side and a connection state of the mobile phase channels to the channel switching valves; and
   a per channel total delivery amount calculation section configured to calculate a total delivery amount of mobile phase per mobile phase channel based on a connection state according to the valve connection state setting section, a delivery amount per unit time by the delivery pump, and an operation time of the delivery pump.

2. The liquid chromatograph according to claim 1, further comprising:
   a per mobile phase total amount setting section configured to set an amount of mobile phase contained in each mobile phase container; and
   a per mobile phase remaining amount calculation section configured to calculate a remaining amount of each mobile phase by subtracting a total delivery amount of mobile phase through each mobile phase channel calculated by the total delivery amount calculation section from the amount of mobile phase in each mobile phase container set in the total amount setting section.

3. The liquid chromatograph according to claim 2,
   wherein the valve connection state setting section is configured to include, as a setting value, connection of two or more mobile phase channels to a common mobile phase container,
   wherein the total delivery amount calculation section is configured to add up, with respect to two or more mobile phase channels connected to the common mobile phase container, total delivery amounts through these mobile phase channels to calculate a total delivery amount of one mobile phase channel, and wherein the remaining amount calculation section is configured to subtract, with respect to the one mobile phase container to which the plurality of mobile phase channels are connected, the total delivery amount obtained by calculation based on addition from the amount of mobile phase in the mobile phase container set in the total amount setting section to calculate a remaining amount of mobile phase in the one mobile phase container to which the plurality of mobile phase channels are connected.

4. The liquid chromatograph according to claim 1, wherein the valve connection state setting section is configured to include, as a setting value, connection of two or more mobile phase channels to a common mobile phase container, and wherein the total delivery amount calculation section is configured to add up, with respect to two or more mobile phase channels connected to the common mobile phase container, total delivery amounts through these mobile phase channels to calculate a total delivery amount of one mobile phase channel.

5. The liquid chromatograph according to claim 1, wherein the channel switching valves have a hierarchical structure including three or more stages.

6. The liquid chromatograph according to claim 1, wherein among the channel switching valves, the channel switching valve on the uppermost stage side is a channel switching valve that is pre-installed in the liquid chromatograph, and a channel switching valve on a second- or later-stage is an optional channel switching valve that is externally attached to the liquid chromatograph.

7. The liquid chromatograph according to claim 1, wherein the channel switching valve has a hierarchical structure including three or more stages, and wherein among the channel switching valves, the channel switching valve on the uppermost stage side is a channel switching valve that is pre-installed in the liquid chromatograph, and a channel switching valve on a second- or later-stage is an optional channel switching valve that is externally attached to the liquid chromatograph.

* * * * *